United States Patent
Kassab et al.

(10) Patent No.: US 8,246,639 B2
(45) Date of Patent: Aug. 21, 2012

(54) ATRAUMATIC CLAMP

(76) Inventors: Ghassan S. Kassab, Zionsville, IN (US); Jose A. Navia, Sr., Buenos Aries (AR)

( * ) Notice: Subject to any disclaimer, the term of this patent is extended or adjusted under 35 U.S.C. 154(b) by 706 days.

(21) Appl. No.: 12/304,253

(22) PCT Filed: Jun. 29, 2007

(86) PCT No.: PCT/US2007/015236
§ 371 (c)(1),
(2), (4) Date: Jul. 15, 2009

(87) PCT Pub. No.: WO2008/005385
PCT Pub. Date: Jan. 10, 2008

(65) Prior Publication Data
US 2012/0109164 A1    May 3, 2012

Related U.S. Application Data

(60) Provisional application No. 60/817,419, filed on Jun. 30, 2006.

(51) Int. Cl.
*A61B 17/08* (2006.01)
(52) U.S. Cl. .......................... 606/158; 606/151; 606/157
(58) Field of Classification Search .................. 606/151, 606/153, 157, 158, 201, 204; 600/9, 12, 600/13, 15; 251/10; 24/66.1, 303; 269/221
See application file for complete search history.

(56) References Cited

U.S. PATENT DOCUMENTS

| | | | |
|---|---|---|---|
| 3,577,583 A | 5/1971 | Amann | |
| 4,016,883 A | 4/1977 | Wright, Jr. | |
| 4,177,813 A | 12/1979 | Miller et al. | |
| 4,447,238 A | 5/1984 | Eldridge, Jr. | |
| 4,531,519 A | 7/1985 | Dunn et al. | |
| 4,542,743 A | 9/1985 | Dunn et al. | |
| 4,681,109 A | 7/1987 | Arroyo | |
| 4,708,140 A | 11/1987 | Baron | |
| 4,715,377 A | 12/1987 | Arroyo | |
| 4,726,372 A | 2/1988 | Perlin | |
| 4,821,719 A | 4/1989 | Fogarty | |
| 4,854,318 A | 8/1989 | Solem et al. | |
| 4,971,055 A | 11/1990 | von Zeppelin | |
| 4,976,721 A | 12/1990 | Blasnik et al. | |
| 5,011,487 A | 4/1991 | Shichman | |
| 5,074,870 A | 12/1991 | von Zeppelin | |
| 5,103,839 A | 4/1992 | Shichman | |
| 5,282,812 A | 2/1994 | Suarez, Jr. | |
| 5,514,147 A | 5/1996 | Hoskin et al. | |
| 5,569,274 A | 10/1996 | Rapacki et al. | |
| 5,571,121 A | 11/1996 | Heifetz | |

(Continued)

OTHER PUBLICATIONS

International Searching Authority, International Search Report, mailed Sep. 3, 2008 (PCT/US2007/015236).

(Continued)

*Primary Examiner* — Julian Woo
(74) *Attorney, Agent, or Firm* — Ice Miller LLP

(57) ABSTRACT

A device for clamping a tissue, the device having a clamp (100) with at least one magnetic portion. In at least one embodiment, the clamp (100) has two oppositely polarized magnets (102, 104) and a mounting structure (106) for the magnets. In some other embodiments, a clamp has an electromagnetic collar (500) and a power source (300) to provide power to the collar (500) via an electrical connector (302). In at least some embodiments, the clamps (100) may also be electromagnetic.

26 Claims, 11 Drawing Sheets

U.S. PATENT DOCUMENTS

| | | |
|---|---|---|
| 5,697,942 A | 12/1997 | Palti |
| 5,725,539 A | 3/1998 | Matern |
| 5,827,170 A | 10/1998 | Gebran |
| 5,897,565 A | 4/1999 | Foster |
| 5,921,996 A | 7/1999 | Sherman |
| 5,928,253 A | 7/1999 | Sherman et al. |
| 6,007,552 A | 12/1999 | Fogarty et al. |
| 6,042,563 A | 3/2000 | Morejohn et al. |
| 6,464,710 B1 | 10/2002 | Foster |
| 7,004,459 B2 * | 2/2006 | Sato et al. .................. 269/221 |
| 7,014,644 B1 | 3/2006 | Bombard et al. |
| 7,144,402 B2 | 12/2006 | Kuester, III |
| 2002/0062065 A1 | 5/2002 | Daniel et al. |
| 2002/0068855 A1 | 6/2002 | Daniel et al. |
| 2002/0183785 A1 | 12/2002 | Howell et al. |
| 2003/0208231 A1 | 11/2003 | Williamson, IV et al. |
| 2004/0133221 A1 | 7/2004 | Sancoff et al. |
| 2004/0143276 A1 | 7/2004 | Sturtz et al. |
| 2006/0100646 A1 | 5/2006 | Hart et al. |
| 2006/0271103 A1 | 11/2006 | Ferrari et al. |

OTHER PUBLICATIONS

International Searching Authority, Written Opinion of the International Searching Authority, completed Aug. 16, 2008 (PCT/US2007/015236).

* cited by examiner

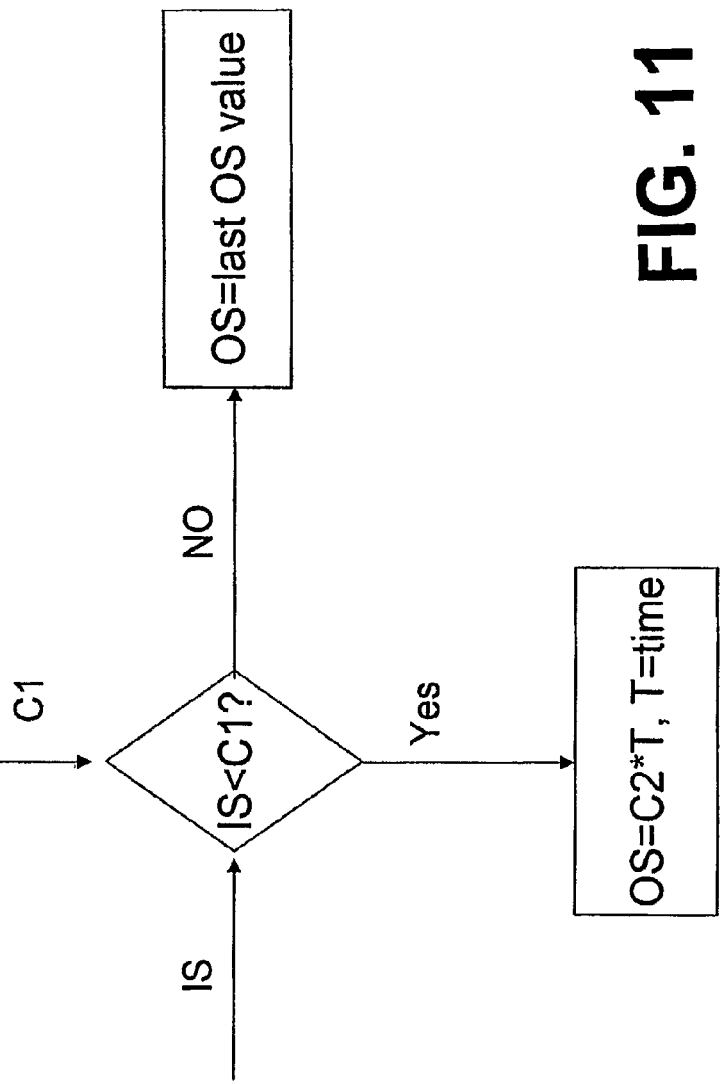

Microcontroller

Assume the input signal (IS) is proportional to the vibration, and the output signal (OS) is proportional to the current in the electromagnetic actuator, the logic of the controller is shown below: C1 is a preset constant represents a threshold for vibration or strain, C2 is the rate of increase in current to control the clamp force when the vibration is below the threshold. Once the clamp exceeds the threshold, the current is maintained constant.

FIG. 11

ATRAUMATIC CLAMP

PRIORITY

The present application is a U.S. National Stage Application of International Patent Application Serial No. PCT/US2007/015236, entitled "ATRAUMATIC CLAMP," filed Jun. 29, 2007, which is related to and claims the benefit of U.S. Provisional Patent Application Ser. No. 60/817,419 filed Jun. 20, 2006, also entitled "ATRAUMATIC CLAMP." The contents of each of these applications are hereby incorporated by reference in their entirety into this disclosure.

BACKGROUND

The disclosure of the present application relates generally to clamps, and more particularly, to atraumatic tissue clamps.

It has been well established that the clamping of blood vessels during surgery may induce injury to endothelium, media, adventitia, vasa vasorum, and baroreceptors. This crushing injury can cause acute events, such as vasospasm, or chronic events, such as endothelial dysfunction, initimal hyperplesia or other undesirable remodeling. In addition, the clamping of calcified blood vessels may result in the crushing of calcium or plaque and dislodging of particles in the blood stream that may lead to vessel obstruction, and consequently, tissue death. These outcomes are a result of design shortcomings associated with conventional clamps. The process of clamping using conventional clamps is invariably asymmetric which leads not only to compressive forces, but also to shear stresses resulting in damage to tissues. An additional shortcoming of conventional clamps is that the magnitude of the forces applied is not controlled or regulated directly by the clamps.

Thus, there is a need in the art for a clamping device and a technique of clamping tissue that does not result in damage to tissue from the potential asymmetric application of stresses to and across the surface of the tissue. The clamping device should be easy to understand and use, universally adoptable, efficient and relatively inexpensive.

SUMMARY

The disclosure of the present application provides devices and methods for clamping tissue atraumatically such that tissue is compressed gently without causing excessive stress or strain. According to at least one embodiment presented herein and throughout this disclosure, reference is made to a blood vessel as an example of a tissue that is used with respect to the disclosure of the present application. However, the disclosure of the present application is not limited to blood vessels (arteries and veins) and may be used within any type of tissue, including, but not limited to, esophageal tissue, gastric tissue, intestine tissue, and bronchial and lung tissue that could benefit from the use of the disclosure of the present application.

The devices described herein may comprise clamping devices that may "mold" to take shape of a particular tissue to be clamped, contrary to a conventional clamp whereby the tissue takes the shape of the clamp itself. In addition, the clamping pressure of the clamping devices described herein may be pre-set for a particular application, eliminating the need, and risks associated therewith, of having a surgeon attempt to predict the required clamping force.

According to at least one embodiment of a device for clamping a tissue of the disclosure of the present application, the device has a clamp with at least one magnetic portion. In at least one embodiment, the clamp has two oppositely polarized magnets and a mounting structure for the magnets. In some other embodiments, a clamp has an electromagnetic collar and a power source to provide power to the collar via an electrical connector. In at least some embodiments, the clamps may also be electromagnetic.

In at least one embodiment, an atraumatic clamp may have at least two oppositely polarized magnets. The magnets may be pliable so that they flex and/or counter in respect to a tissue being clamped. An atraumatic clamp may also have a mounting structure for the magnets. A magnetic force may bias the electromagnets toward each other, thereby exerting a clamping pressure on the tissue.

In at least one embodiment, a device may also have a power source for providing power to the electromagnets, and an electrical connector coupled to the power source and the electromagnets. Power may be provided by the power source through the electrical connector to electrify at least one of the electromagnets, causing the clamps to clamp a tissue. A device may also have a sensor coupled to the electromagnets, whereby the sensor is operable to detect the level of clamping pressure upon a tissue being clamped. A device may also have a control mechanism coupled to the power source and the sensor, and the control mechanism operable to regulate the power level from the power source used to electrify the electromagnets.

In at least one embodiment, an atraumatic clamp has an electromagnetic collar and a power source to provide power to the collar via an electrical connector. The collar may also be electromagnetic. The collar may be pliable so that they flex and/or counter in respect to a tissue being clamped. In at least one embodiment, a device may also have a power source for providing power to the collar, and an electrical connector coupled to the power source and the collar. Power may be provided by the power source through the electrical connector to electrify an electromagnetic collars, causing the collar to clamp a tissue. A device may also have a sensor coupled to the collar, whereby the sensor is operable to detect the level of clamping pressure upon a tissue being clamped. A device may also have a control mechanism coupled to the power source and the sensor, and the control mechanism operable to regulate the power level from the power source used to electrify the electromagnetic collar. The control mechanism may also direct the power source to maintain a present level of power when the clamping pressure detected by a sensor meets or exceeds a predetermined threshold.

According to at least one embodiment of a method for clamping tissue of the disclosure of the present application, the method has the steps of providing a clamp for clamping tissue according to at least one of the aforementioned embodiments, positioning the clamp around a tissue, and clamping the tissue by exerting a force from the clamp on the tissue.

BRIEF DESCRIPTION OF THE DRAWINGS

FIG. 11 shows a diagram of the functionality of a microcontroller according to at least one embodiment of the present disclosure.

DETAILED DESCRIPTION

Figure 1A:
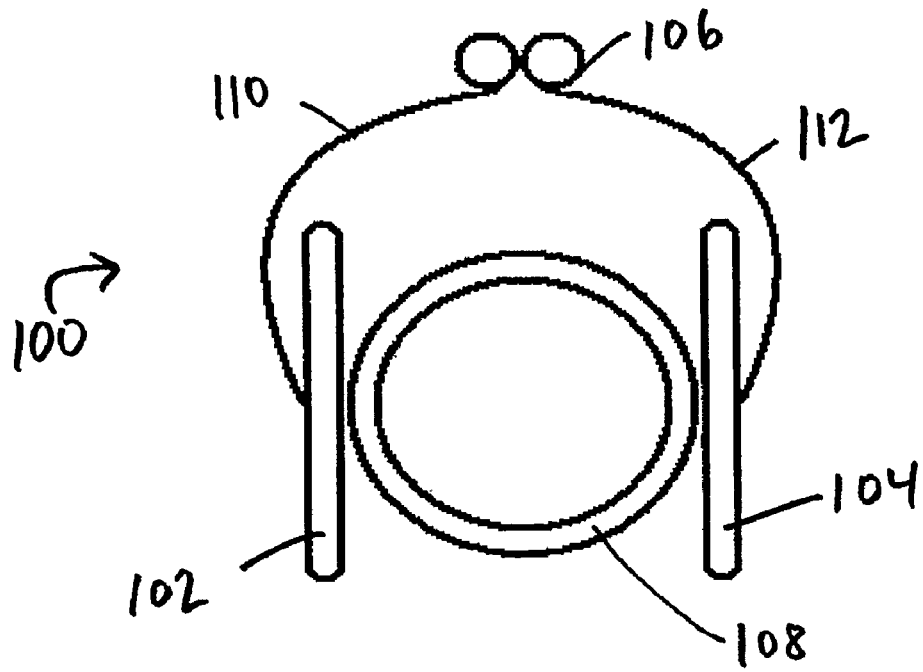
FIG. 1A shows an atraumatic clamp according to at least one embodiment of the present disclosure engaging a healthy tissue.

The present disclosure relates to atraumatic tissue clamps and the use of said clamps for clamping various vessels and tissues. For the purposes of promoting an understanding of the principles of the present disclosure, reference will now be made to the embodiments illustrated in the drawings, and specific language will be used to describe the same. It will nevertheless be understood that no limitation of the scope of the present disclosure is thereby intended.

A basic premise of the present disclosure, and the exemplary embodiments of devices, systems and methods described herein, is to minimize the excessive and potentially damaging external stresses and strains that are imposed on a tissue during clamping, thereby minimizing any potential damage to the tissue.

An atraumatic clamp according to at least one embodiment of the disclosure of the present application is shown in FIG. 1A. In the embodiment shown in FIG. 1A, atraumatic clamp 100 comprises first magnet 102 and second magnet 104, whereby first magnet 102 and second magnet 104 are coupled to one another by a mounting structure 106. In at least one embodiment, atraumatic clamp 100 comprises two magnets. In an additional embodiment, atraumatic clamp 100 comprises three or more magnets.

First magnet 102 and second magnet 104 comprise magnets with opposing polarities so that the inner surfaces of first magnet 102 and second magnet 104 attract to one another. A magnetic force between first magnet 102 and second magnet 104 attracts first magnet 102 to second magnet 104, noting that the magnetic force may be relatively opposite to a hinge force exerted by the mounting structure 106. First magnet 102 and second magnet 104 may be of any size and/or shape as may be useful with the disclosure of the present application to exert clamping pressure on tissue 108. Tissue 108, intended to encompass a "vessel" as described herein, may be positioned substantially in between first magnet 102 and second magnet 104, whereby a magnetic force between first magnet 102 and second magnet 104 bias the magnets toward each other thereby exerting a clamping pressure on tissue 108.

The size and/or shape of first magnet 102 and second magnet 104 may be tailored to a particular clamping application. In addition, a user of atraumatic clamp 100 may be able to "dial-in" a particular clamping force of first magnet 102 and second magnet 104 by adjusting mounting structure 106, by selecting first magnet 102 and/or second magnet 104 of a particular size and/or shape for the intended application, or by regulating power as described herein.

Additionally, first magnet 102 and/or second magnet 104 may be pliable, i.e. first magnet 102 and/or second magnet 104 may flex and/or contour in respect to a particular tissue 108 positioned substantially in between first magnet 102 and second magnet 104. According to at least one embodiment, first magnet 102 and second magnet 104 of atraumatic clamp 100 comprise pliable magnets. In at least one embodiment, the surface of first magnet 102 and/or second magnet 104 may be coarse, similar to the texture of sandpaper, to minimize slippage of tissue 108 clamped between first magnet 102 and second magnet 104 of atraumatic clamp 100.

Mounting structure 106 of atraumatic clamp 100 may comprise a first arm 110 and a second arm 112 each having a distal end. First arm 110 may be hingedly coupled to first magnet 102 at or near its distal end and second arm 112 may be hingedly coupled to second magnet 104 at or near its distal end. Mounting structure 106 may exert a hinge force causing the distal ends of first arm 110 and second arm 112 to extend away from one another. In at least one embodiment, atraumatic clamp 100 comprises one contiguous unitary arm instead of first arm 110 and second arm 112.

Atraumatic clamp 100 may comprise magnetic material to clamp the vessel symmetrically and gently. The magnetic mechanism of closure or clamp of the vessel minimizes the damage to the vessel. The magnetic clamp force is sufficient to provide the closure force in the presence of physiological pressure.

Figure 1B:
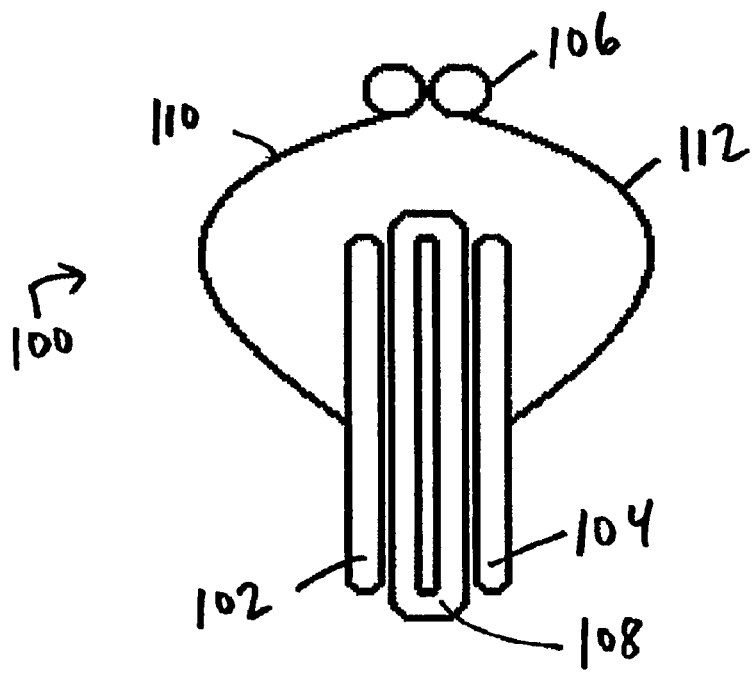
FIG. 1B shows an atraumatic clamp according to at least one embodiment of the present disclosure compressing a healthy tissue.

FIG. 1B shows an embodiment of atraumatic clamp 100 of the present disclosure compressing a tissue 108. Tissue 108, as shown in FIGS. 1A and 1B, is a blood vessel, with the blood vessel in a "normal" or "unclamped" state in FIG. 1A, and in a "restricted" or "clamped" state in FIG. 1B. First magnet 102 and second magnet 104 may symmetrically compress tissue 108 with a predetermined force. In this fashion, atraumatic clamp 100 may exert clamping pressure on tissue 108. In this instance, the mode of deformation of tissue 108 does not involve significant shearing of tissue 108 and hence is relatively atraumatic.

In an exemplary embodiment of the present disclosure shown in FIG. 1, first magnet 102 and second magnet 104 are connected through mounting structure 106 to symmetrically compress tissue 108 with a predetermined force. This mode of deformation does not involve significant shearing of tissue 108 and hence is relatively atraumatic. Such a minimal force may be predetermined experimentally for different size tissues 108. In a situation where a tissue 108 is a vessel, atraumatic clamp 100 does not need to completely close the vessel in order to restrict the flow of blood through a vessel as necessary. Near closure of a vessel may cause fluid-solid (blood-vessel) interactions leading to vibrations of a vessel wall. This model of vibration (the small temporal fluctuation of vessel diameter) occurs immediately before full closure of a vessel. These vibrations can be detected by a sensor (e.g., strain gauge) which would then feed back to a control mechanism to control one or more atraumatic clamps 100 to maintain the force (through the electrical current) at that sensed level of closure. In this example, the majority of flow (99%) would essentially be arrested without completely closing the vessel to avoid trauma of the vessel. Notwithstanding the foregoing, and as may be preferred, atraumatic clamps 100 may be completely closed as to fully restrict the flow of blood through a vessel as desired.

Figure 2:
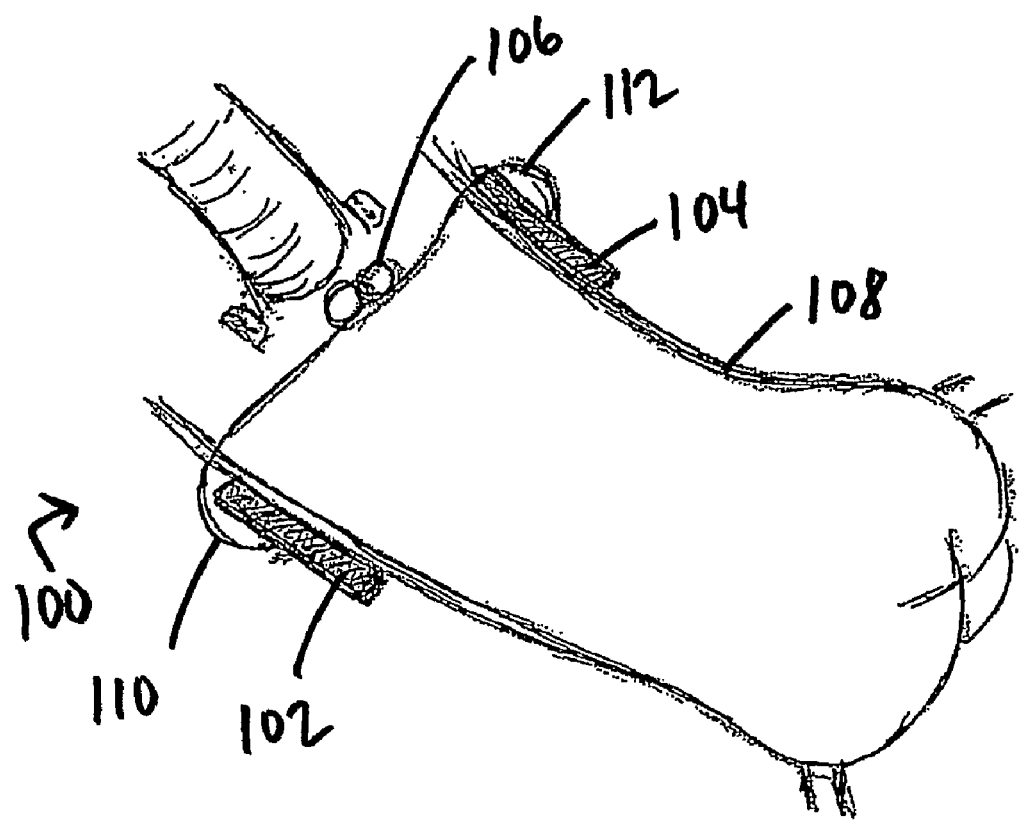
FIG. 2 shows an atraumatic clamp according to at least one embodiment of the present disclosure engaging a healthy tissue.

FIG. 2 shows an embodiment of atraumatic clamp 100 of the present disclosure engaging a tissue 108 (for example, an ascending aorta). As shown in FIG. 2, first magnet 102 is positioned on one side of tissue 108, and second magnet 104 is positioned on the opposite side of tissue 108. In this fashion, atraumatic clamp 100 may exert clamping pressure on tissue 108.

Figure 3A:
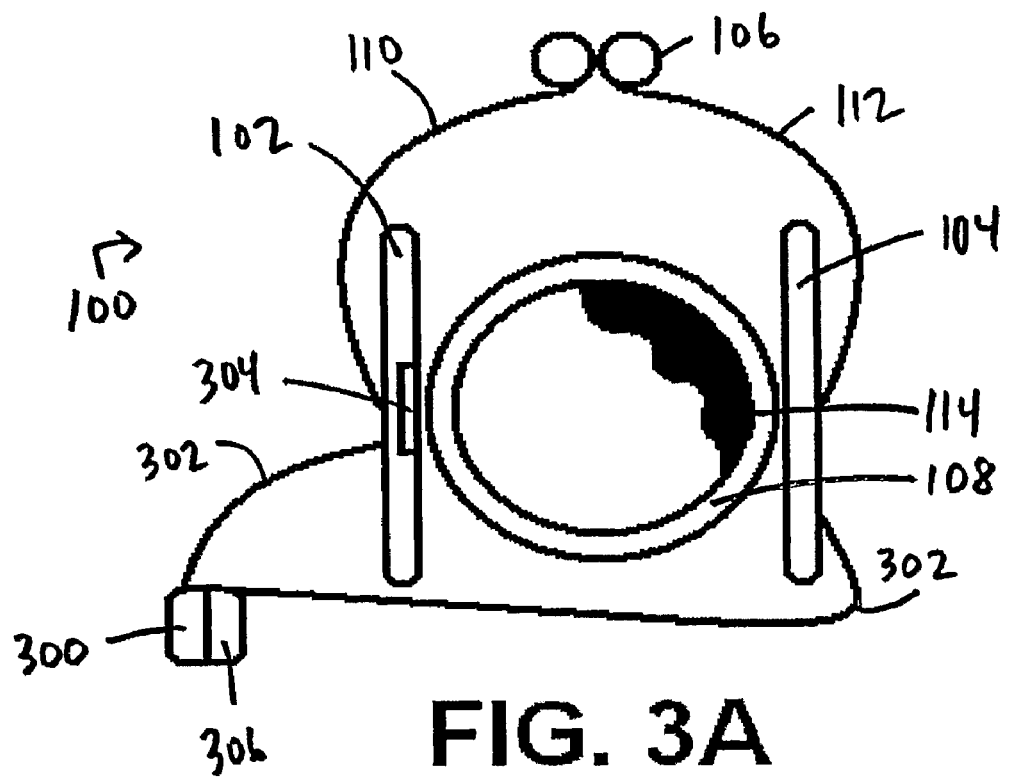
FIG. 3A shows an atraumatic clamp according to at least one embodiment of the present disclosure engaging a diseased or calcified tissue.
Figure 3B:
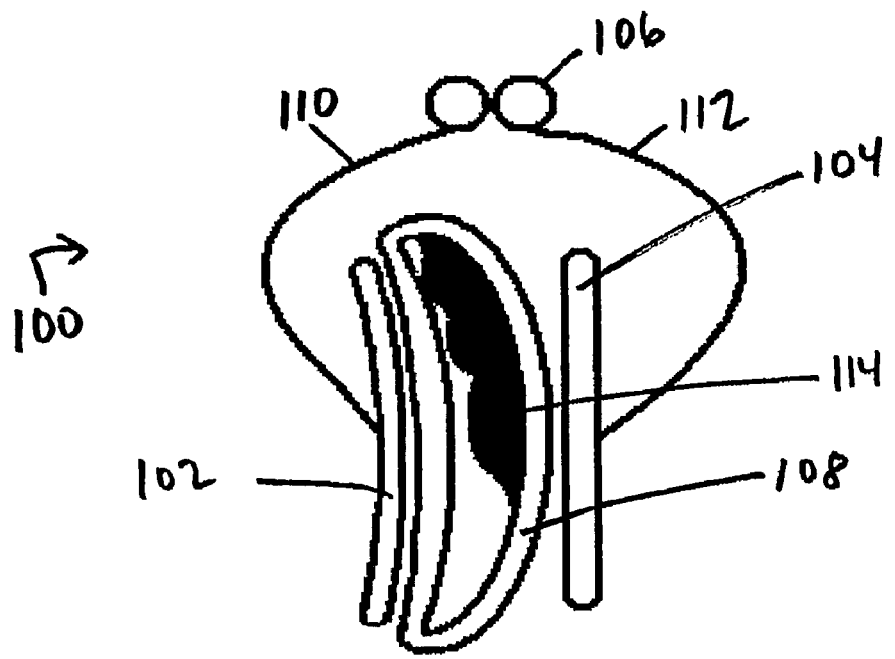
FIG. 3B shows an atraumatic clamp compressing a diseased or calcified tissue according to at least one embodiment of the present disclosure.

An atraumatic clamp 100 according to at least one embodiment of the disclosure of the present application is shown in FIG. 3A. In the embodiment shown in FIG. 3A, similar to the embodiment shown in FIG. 1A, atraumatic clamp 100 comprises first magnet 102 and second magnet 104, whereby first magnet 102 and second magnet 104 are coupled to one another by mounting structure 106. In this embodiment of atraumatic clamp 100, mounting structure 106 comprises first arm 110 and second arm 112. First arm 110 is hingedly coupled to first magnet 102 and second arm 114 may be hingedly coupled to second magnet 104. Mounting structure 106 may exert a hinge force causing the distal ends of first arm 110 and second arm 112 to extend away from one another. However, and as shown in FIGS. 3A, and 3B, tissue 108 to be clamped by atraumatic clamp 100 represents a diseased or calcified vessel.

In the case of a diseased or calcified vessel, the deformation of the vessel may be asymmetric, but the asymmetric deformation will avoid excessive compression of at least one vessel particle 114, e.g., plaque or calcium, present within the diseased or calcified vessel. According to at least one embodiment of atraumatic clamp 100, the force is identical on the two poles or plates, but the deformation depends on the elasticity of a vessel. The softer, non-diseased portion of a vessel may deform towards the diseased wall of the vessel as shown in FIG. 3B. This will minimize the use of excessive force that may cause breakage of at least one vessel particle 114 present within a vessel.

In at least one embodiment of the present disclosure, atraumatic clamp 100 may utilize electromagnetic current. An example of an atraumatic clamp 100 utilizing electromagnetic current is shown in FIG. 3A. Atraumatic clamp 100 may be "automated", or made "smart", by the use of electromagnetic current flowing from a power source 300 for providing power through at least one electrical connector 302. Electrical connectors 302 may be operably coupled between power source 300 and first magnet 102, and another electrical connector 302 may be operably coupled between power source 300 and second magnet 104. In such an embodiment, first magnet 102 and second magnet 104 are electromagnets.

Power source 300 may operate to provide power to at least one magnet (first magnet 102, second magnet 104, etc.) through electrical connector 302, causing atraumatic clamp 100 to clamp a tissue positioned therebetween.

In such an embodiment, magnetic force is induced through an electric current. Hence, a power driven device may regulate the degree of force required to close a particular tissue 108, like a blood vessel, minimally. Such an embodiment (as discussed herein) may also sense information on the pressure, stress or strain (deformation) of the vessel to regulate the degree of force.

As shown in the embodiment of FIG. 3A, atraumatic clamp 100 may further comprise at least one sensor 304 operably coupled to at least one magnet (first magnet 102, second magnet 104, etc.). Sensor 304 may operate to detect the level of clamping pressure upon tissue 108 positioned substantially in between at least two of the magnets.

As shown in FIG. 3A, atraumatic clamp 100 may also comprise at least one control mechanism 306 operably coupled to the power source 300 and sensor 304, the control mechanism 306 is operable to regulate the level of power provided by power source 300 used to electrify at least one of the magnets (first magnet 102, second magnet 104, etc.). Atraumatic clamp 100 may comprise both sensor 304 and control mechanism 306 simultaneously.

According to at least one embodiment of atraumatic clamp 100, control mechanism 306 may be operably coupled to power source 300. In such an embodiment, control mechanism 306 may direct power source 300 to maintain the present level of power when the clamping pressure detected by sensor 304 meets or exceeds a predetermined threshold.

According to at least one embodiment of atraumatic clamp 100, at least one sensor 304 is operably coupled to control mechanism 306 and is operable to detect a strain in tissue 108. Vessel wall vibrations (as previously discussed) may be a time-varying strain or deformation. Such vibrations of the vessel wall may be detected by sensor 304, which may be an electrical circuit (i.e., Wheatstone bridge), in contact with atraumatic clamp 100. Additional methods to amplify the vibrations to detect the sound waves, similar in principle to microphone amplification, are within the spirit of the present disclosure. In such an embodiment, control mechanism 306 is operable to regulate the level of power provided by power source 300 based upon a level of strain detected in tissue 108 by sensor 304. Such a feedback loop from sensor 304 to control mechanism 306 allows atraumatic clamp 104 to maintain a desired clamping pressure upon tissue 108.

Figure 10:
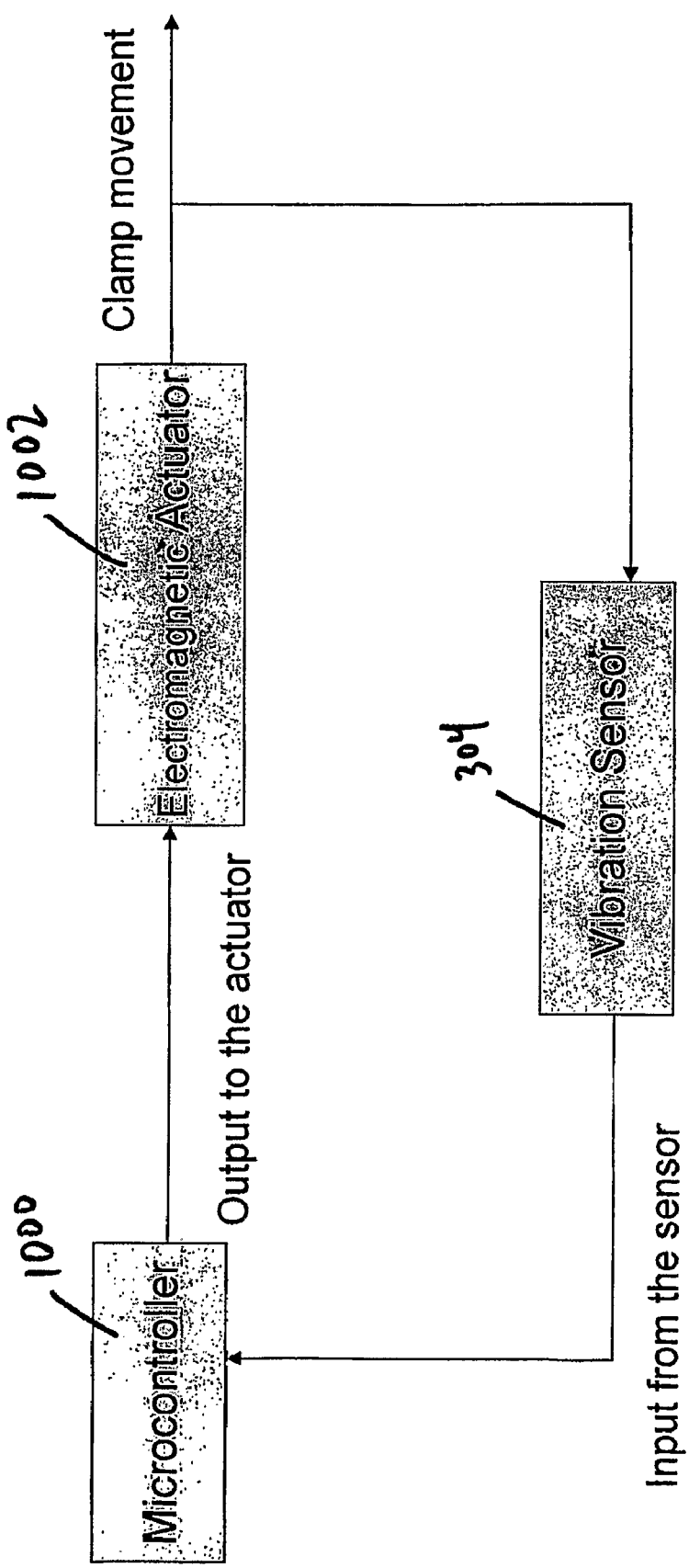
FIG. 10 shows a diagram of the components of a control mechanism according to at least one embodiment of the present disclosure.

In at least one embodiment, a combination of hardware and software to operate control mechanism 306 according to the foregoing is within the scope and spirit of the disclosure of the present application. As shown in FIG. 10, and in at least one embodiment, control mechanism 306 may comprise a microcontroller 1000 to provide output to an electromagnetic actuator 1002 to control the clamping movement of atraumatic clamp 100 and/or magnetic/electromagnetic collar (as described below). Sensor 304, shown as "Vibration Sensor" in FIG. 10, may provide feedback information to microcontroller 1000 based upon information detected by sensor 304.

An example of the functionality of microcontroller 1000 is shown in FIG. 11. In this example, an assumption is made that an input signal (IS) is proportional to a vibration (as described above), and an output signal (OS) is proportional to a current in electromagnetic actuator 1002. In this example, the logic is shown in the diagram portion of FIG. 11, wherein C1 is a preset constant representing a threshold for vibration or strain, C2 is a rate of increase in current to control atraumatic clamp 100 and/or a magnetic/electromagnetic collar (as described below) force when the vibration is below the preset vibration threshold. Once a clamping device exceeds the threshold, the current/power to the clamping device is maintained constant.

According to at least one embodiment of atraumatic clamp 100, sensor 304 comprises multiple sensors operably coupled to at least one of the magnets (first magnet 102, second magnet 104, etc.). In such an embodiment, sensors 304 may detect clamping pressure and strain in tissue 108.

Figure 4:
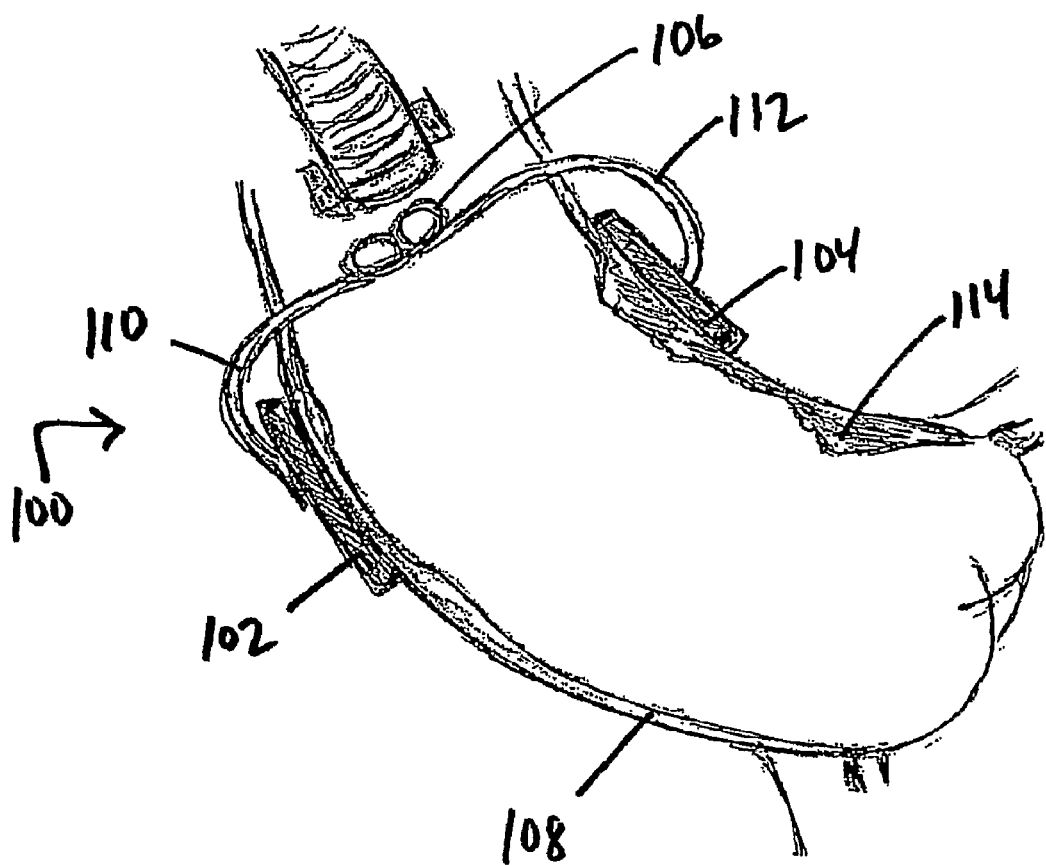
FIG. 4 shows an atraumatic clamp according to at least one embodiment of the present disclosure engaging a diseased or calcified tissue.

FIG. 4 shows an embodiment of atraumatic clamp 100 of the present disclosure clamping a diseased or calcified tissue 108 (for example, a calcified ascending aorta) having at least one vessel particle 114 within tissue 108. As shown in FIG. 2, first magnet 102 is positioned on one side of tissue 108, and second magnet 104 is positioned on the opposite side of tissue 108. In this fashion, atraumatic clamp 100 may exert clamping pressure on tissue 108.

Figure 5:
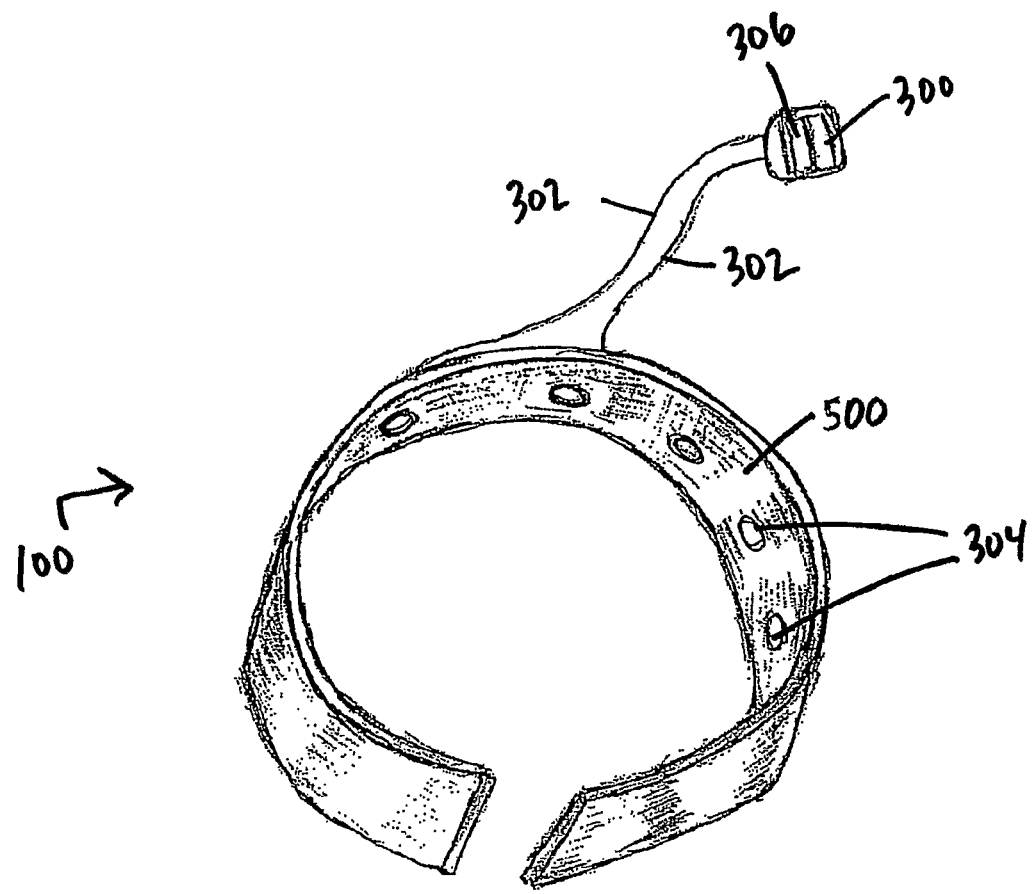
FIG. 5 shows an atraumatic clamp according to at least one embodiment of the present disclosure.

An atraumatic clamp according to at least one embodiment of the disclosure of the present application is shown in FIG. 5. In the embodiment shown in FIG. 5, atraumatic clamp 100 comprises at least one magnetic collar 500 and power source 300 for providing power through electrical connector 302. Electromagnetic collar 500 may be pliable, i.e., electromagnetic collar 500 may flex and/or contour in respect to a particular tissue 108 positioned substantially within electromagnetic collar 500. Tissue 108 may be positioned substantially within electromagnetic collar 500, whereby a magnetic force within electromagnetic collar 500 exerts a clamping pressure on tissue 108. Electromagnetic collars 500 may have a gap within electromagnetic collar 500 (as shown in FIG. 5) to allow tissue 108 to be positioned substantially within. Electromagnetic collar 500 may be of any size and/or shape as may be useful with the disclosure of the present application to exert clamping pressure on tissue 108.

Power source 300 may operate to provide power to electromagnetic collar 500 through electrical connector 302, causing electromagnetic collar 500 to clamp a tissue positioned therebetween.

Figure 6A:
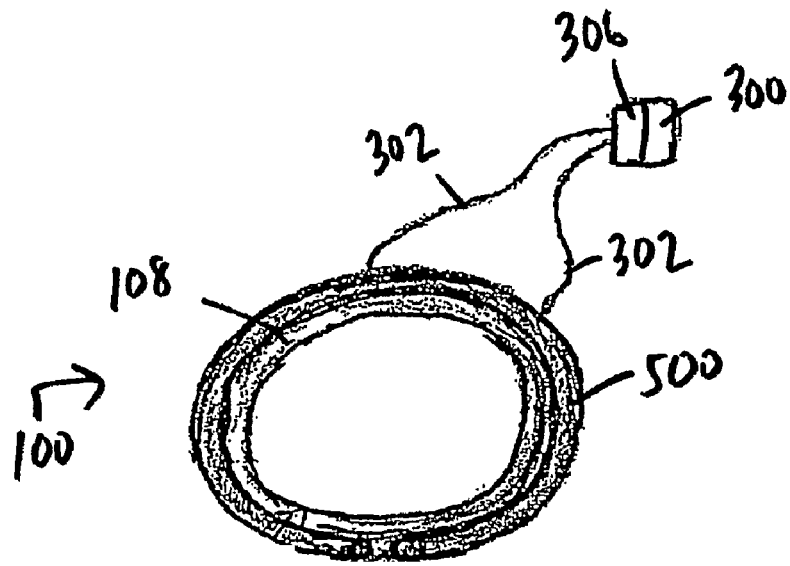
FIG. 6A shows an atraumatic clamp according to at least one embodiment of the present disclosure engaging a healthy tissue.
Figure 6B:
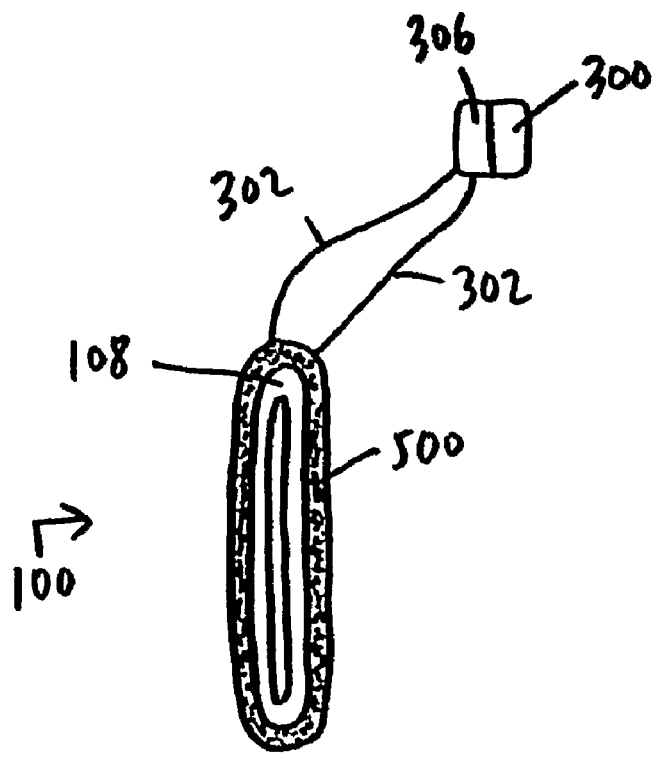
FIG. 6B shows an atraumatic clamp according to at least one embodiment of the present disclosure compressing a healthy tissue.

FIGS. 6A and 6B show an embodiment of an atraumatic clamp 100 of the present disclosure engaging tissue 108. Tissue 108, as shown in FIGS. 6A and 6B, is a blood vessel, with the blood vessel in a "normal" or "unclamped" state in FIG. 6A, and in a "restricted" or "clamped" state in FIG. 6B. Electromagnetic collar 500 may compress tissue 108 with a predetermined force. In this instance, the mode of deformation of tissue 108 does not involve significant shearing of tissue 108 and hence is relatively atraumatic.

The size and/or shape of electromagnetic collars 500 may be tailored to a particular clamping application. In addition, a user of electromagnetic collars 500 may be able to "dial-in" a particular clamping force by selecting electromagnetic collars 500 of a particular size and/or shape for the intended application or by regulating power as described herein.

Figure 7A:
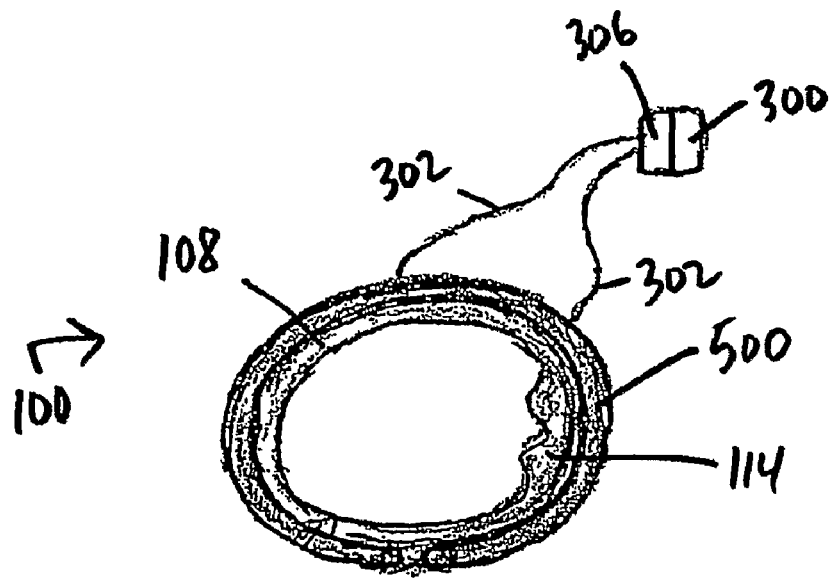
FIG. 7A shows an atraumatic clamp according to at least one embodiment of the present disclosure engaging a diseased or calcified tissue.
Figure 7B:
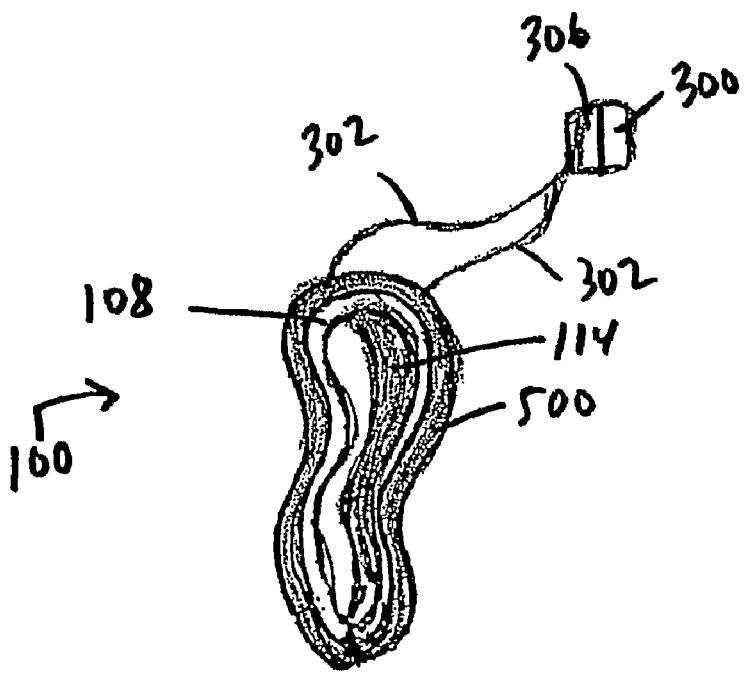
FIG. 7B shows an atraumatic clamp according to at least one embodiment of the present disclosure compressing a diseased or calcified tissue.

An atraumatic clamp 100 according to at least one embodiment of the disclosure of the present application is shown in FIGS. 7A and 7B. In the embodiment shown in FIGS. 7A and 7B, similar to the embodiment shown in FIGS. 5A and 5B, atraumatic clamp 100 comprises electromagnetic collar 500 and power source 300 for providing power through at least one electrical connector 302. However, and as shown in FIGS. 5A, and 5B, tissue 108 to be clamped by atraumatic clamp 100 represents a diseased or calcified vessel having at least one vessel particle 114 present within the diseased or calcified vessel.

In a situation wherein a tissue 108 is a vessel, electromagnetic collars 500 do not need to completely close the vessel in order to restrict the flow of blood through a vessel as necessary. As discussed above, near closure of a vessel may cause fluid-solid (blood-vessel) interactions leading to vibrations of a vessel wall. This model of vibration (the small temporal fluctuation of vessel diameter) occurs immediately before full closure of a vessel. These vibrations can be detected by a sensor (e.g., strain gauge) which would then feed back to a control mechanism to control one or more electromagnetic collars 500 to maintain the force (through the electrical current) at that sensed level of closure. In this example, the majority of flow (99%) would essentially be arrested without completely closing the vessel to avoid trauma of the vessel. However, and as may be preferred regarding an actual excision of tissue 112 as described herein, electromagnetic collars 500 may be completely closed as to fully restrict the flow of blood through a vessel as desired.

In at least one embodiment of the present disclosure, atraumatic clamp 100 may utilize electromagnetic current. An example of an atraumatic clamp 100 utilizing electromagnetic current is shown in FIGS. 5-7B. As shown in FIGS. 5-7B, atraumatic clamp 100 may be "automated", or made "smart", by the use of electromagnetic current flowing from power source 300 for providing power through electrical connector 302. Electrical connectors 302 may be operably coupled between power source 300 and electromagnetic collar 500. In such an embodiment, magnetic force is induced through an electric current. Hence, a power driven device may regulate the degree of force required to close a particular tissue 108, like a blood vessel, minimally. Such an embodiment (as discussed herein) may also sense information on the pressure, stress or strain (deformation) of the vessel to regulate the degree of force.

According to at least one embodiment of atraumatic clamp 100, two electrical connectors 302 comprising ferromagnetic bars may be interspersed along the circumference of electromagnetic collar 500. In such an embodiment, two electrical connectors 302 form the inductors (magnetic dipoles) when the electric current is applied. The magnetic dipoles on the two hemispheres (or halves of the circumference of electromagnetic collar 500) are used to control the force, which is used to compress tissue 108.

As shown in the embodiment of FIG. 5, atraumatic clamp 100 may further comprise at least one sensor 304 operably coupled to electromagnetic collar 500. Sensor 304 may operate to detect the level of clamping pressure upon tissue 108 positioned substantially within at least one electromagnetic collar 500. According to at least one embodiment of atraumatic clamp 100 and/or electromagnetic collar 500, one may prefer to very the force on tissue 108 locally as to locally deform tissue 108 depending on the circumferential distribution of plaque around the vessel. The concept is not to force a damaged tissue 108, for example a calcified aorta, to take on the shape of a rigid clamp, as that may cause disruption and fracture of the plaque regions within damaged tissue 108. Instead, it may be preferred that the clamp, for example atraumatic clamp 100 and/or electromagnetic collar 500, would take on the shape of tissue 108 being clamped. If the force is controlled at each sensor 304 site, then soft tissue 108 (having no plaque) may deform more than at the location of calcified plaque tissue 108. In this way, atraumatic clamp 100 and/or electromagnetic collar 500 may cause little deformation to the calcified regions and deform the soft portions of tissue 108 towards the rigid portion.

As shown in FIGS. 5-7B, atraumatic clamp 100 may also comprise at least one control mechanism 306 operably coupled to the power source 300, the control mechanism 306 is operable to regulate the level of power provided by power source 300 used to electrify at least one of the magnet(s) of electromagnetic collar 500. Atraumatic clamp 100 may comprise both sensor 304 and control mechanism 306 simultaneously.

According to at least one embodiment of atraumatic clamp 100, including but not limited to the embodiment shown in FIG. 5, control mechanism 306 may be operably coupled to power source 300. In such an embodiment control mechanism 306 may direct power source 300 to maintain the present level of power when the clamping pressure detected by sensor 304 meets or exceeds a predetermined threshold.

Figure 8:
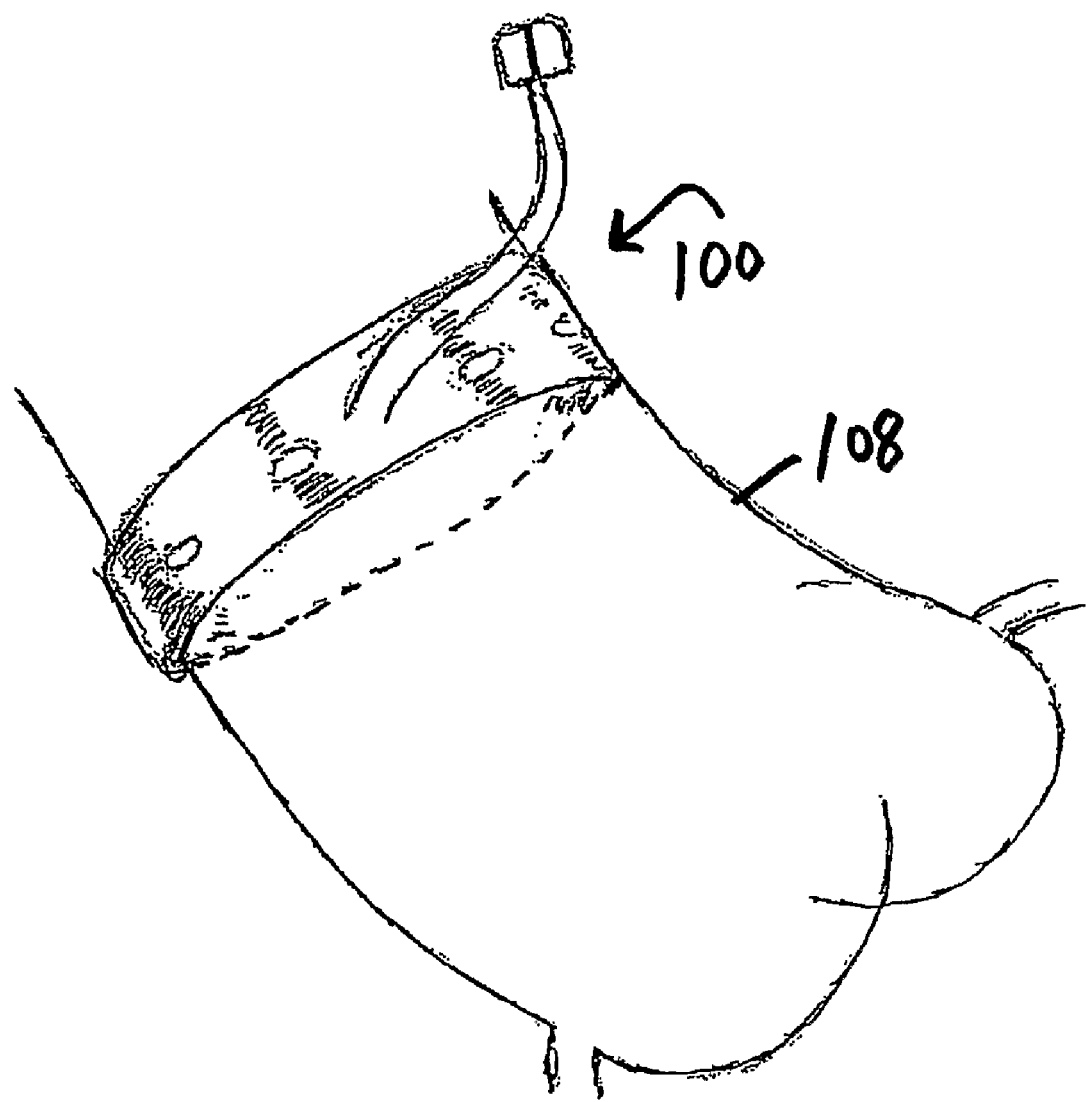
FIG. 8 shows an atraumatic clamp according to at least one embodiment of the present disclosure engaging a tissue.
Figure 9A:
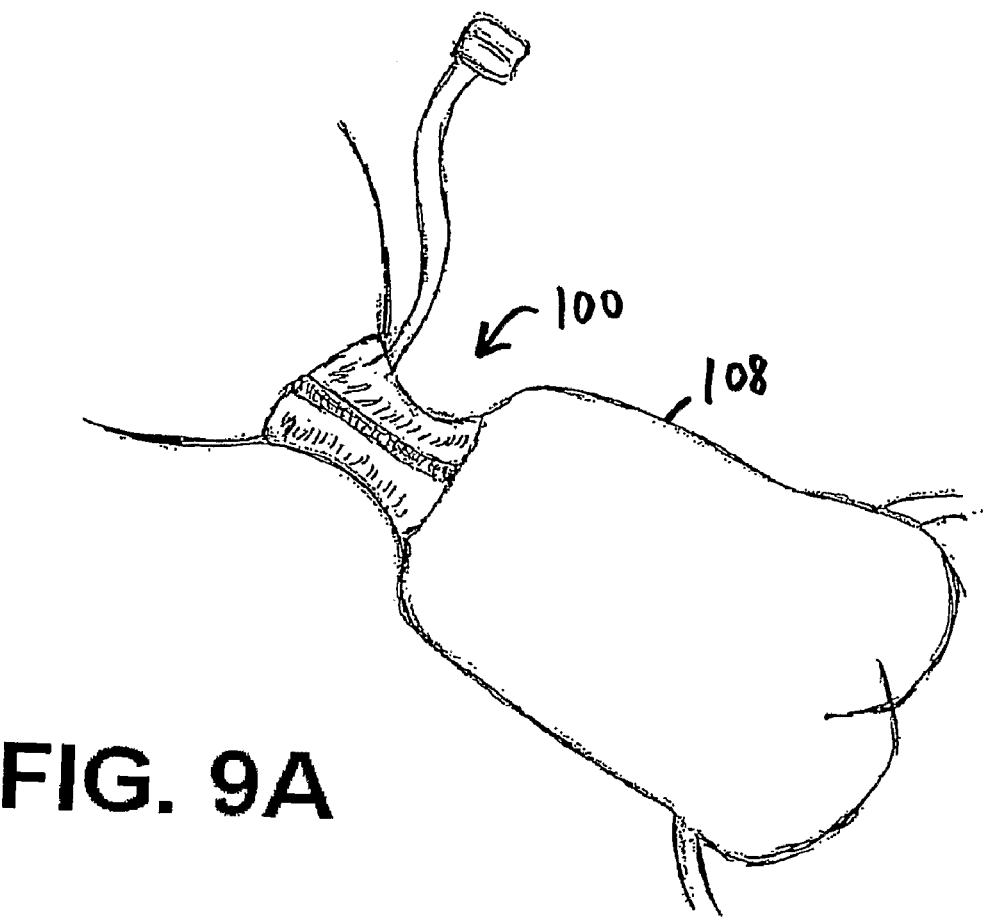
FIG. 9A shows an atraumatic clamp according to at least one embodiment of the present disclosure exerting moderate clamping pressure on a tissue.
Figure 9B:
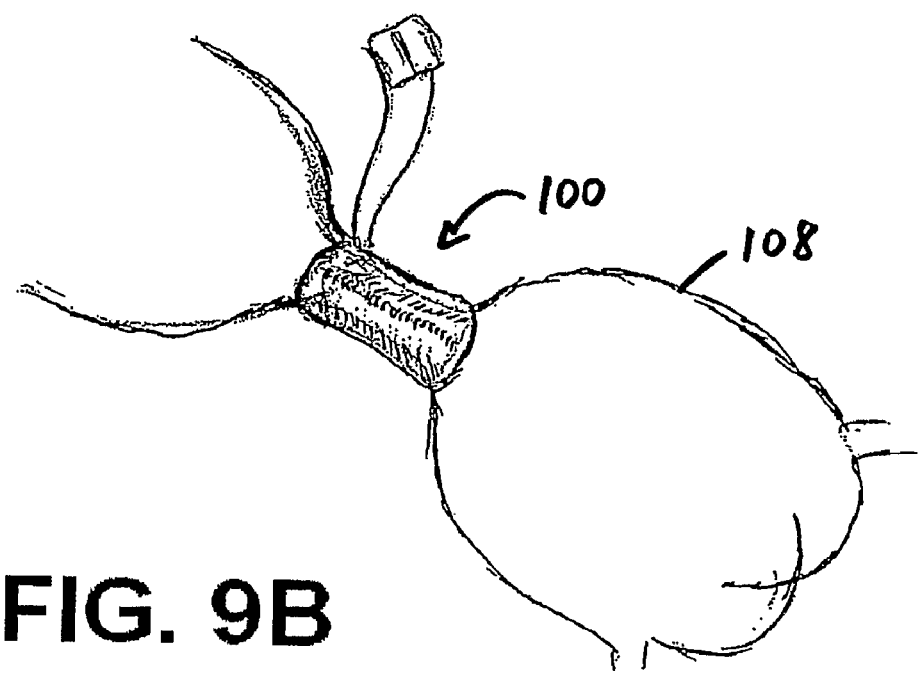
FIG. 9B shows an atraumatic clamp according to at least one embodiment of the present disclosure exerting high clamping pressure on a tissue.

FIG. 8 shows an embodiment of atraumatic clamp 100 of the present disclosure clamping a tissue 108. As shown in FIG. 8, electromagnetic collar 500 is positioned around tissue 108, and in this fashion, atraumatic clamp 100 may exert clamping pressure on tissue 108. FIG. 8 shows an embodiment of atraumatic clamp 100 positioned around tissue 108 and either not exerting clamping pressure or only exerting minimal clamping pressure, while FIGS. 9A and 9B show an embodiment of atraumatic clamp 100 exerting moderate and high pressure on tissue 108, respectively.

According to at least one embodiment of atraumatic clamp 100, sensor 304 is operable to detect a strain in tissue 108. As discussed above, vessel wall vibrations may be a time-varying strain or deformation. Such vibrations of the vessel wall may be detected by sensor 304, which may be an electrical circuit (i.e., Wheatstone bridge), in contact with electromagnetic collar 500. Additional methods to amplify the vibrations to detect the sound waves, similar in principle to microphone amplification, are within the spirit of the present disclosure. In such an embodiment, control mechanism 306 is operable to regulate the level of power provided by power source 300 based upon a level of strain detected in tissue 108 by sensor 304. Such a feedback loop from sensor 304 to control mechanism 306 allows electromagnetic collar 500 to maintain a desired clamping pressure upon tissue 112.

In at least one embodiment of atraumatic clamp 100, sensor 304 comprises multiple sensors 304 operably coupled to electromagnetic collar 500. In such an embodiment, sensors 304 may detect clamping pressure and strain in tissue 108.

One or more at least one or more sensors 304, as discussed herein, may be used to sense pressure, stress or strain (deformation) on tissue 108 being clamped. A force is increased through an increase in current which is balanced again by sensing pressure or deformation of tissue 108. The force may be maintained at the point of critical closure, defined as the instance where there is an equilibrium between the applied force and the hemodynamic-elastic force. At the point of critical closure, atraumatic clamp 100 and/or an atraumatic clamp 100 control system may sense a "vibration" to indicate the critical closure point. In a calcified or damaged tissue 108, for example a calcified blood vessel, the blood vessel is deformed along the non-diseased portion. If the majority of the vessel circumference is diseased, the force required to compress the vessel may become unacceptably large, and the current may be cut off as predetermined by a preset upper limit on force. This may prevent the crushing of the plaque within tissue 108.

This principle can also be used to decide the area of calcification. A force is generated through the system disclosed herein and the corresponding deformation is recorded. Through variation of force, a force-length or stress-strain relation may be determined using one or more sensors 304 to provide a circumferential profile of compliance or stiffness of tissue 108 which is an indication of health or disease of a particular tissue 108. The data can be represented visually in terms of compliance, elasticity, stiffness, etc. These or similar parameters may be displayed in color circumferentially along a tissue 108 to give a surgeon indications of regions of calcification or plaque. In at least one embodiment, the data on the stiffness modulus (the change in strain over the change in stress) along the vessel circumference can be exported from an electronic spreadsheet, such as, for example, an Excel file, to AutoCAD where the software uses the data coordinates to render a color-map on a monitor.

Permanent magnets of the present disclosure to be selected may be thin, smooth ferromagnetic bars. The saturation hysteresis loop is an important feature for a permanent magnet material. During the process of magnetizing the sample, the magnet is subjected to a field that produces a flux density close to saturation. When the magnetizing field is reduced to zero, the induction drops back to a value. If the magnetizing field is reversed, the magnetic poles of the thin smooth ferromagnetic bars are reversed. According to at least one embodiment of atraumatic clamp 100, a user may select the specific magnetic field (Tesla) desired for a particular application through appropriate magnetic material. This selection, in conjunction with the design of geometry (dimensions) of a particular magnet (of atraumatic clamp 100 and/or electromagnetic collar 500), a user may determine the appropriate magnetic forces for the vessel or tissue 108 of interest, i.e., a larger force for a larger vessel.

With a wide variation of properties available in permanent magnet materials, the following criteria may be used to specify the optimum material for a device of the present application: (1) Application-Magnetic Field Requirement; (2) Physical or Mechanical-Space Factor, Weight; (3) Stability Requirements; (4) Ductility Requirements; (5) Biocompatibility; and (6) Costs.

It can be appreciated that any number of tissues 108, including but not limited to, veins, arteries, esophageal tissue, gastric tissue, intestine tissue, and bronchial and lung tissue may benefit from the application of an atraumatic clamp 100 of the present disclosure.

It can also be appreciated that a vessel may not need to be completely closed in order for atraumatic clamp 100 to function as desired. For example, and depending on the size of a vessel to be clamped, a gap of approximately 100 microns may be small enough to restrict the flow of blood through a vessel to allow for a surgeon to proceed with a surgical procedure.

The foregoing disclosure of the exemplary embodiments of the present application has been presented for purposes of illustration and description and can be further modified within the scope and spirit of this disclosure. It is not intended to be exhaustive or to limit the present disclosure to the precise forms disclosed. This application is therefore intended to cover any variations, uses, or adaptations of a device, system and method of the present application using its general principles. Further, this application is intended to cover such departures from the present disclosure as may come within known or customary practice in the art to which this system of the present application pertains. Many variations and modifications of the embodiments described herein will be apparent to one of ordinary skill in the art in light of the above disclosure. The scope of the present disclosure is to be defined only by the claims appended hereto, and by their equivalents.

Further, in describing representative embodiments of the present disclosure, the specification may have presented the method and/or process of the present disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present disclosure should not be limited to the performance of their steps in the order written, and one skilled in the art can readily appreciate that the sequences may be varied and still remain within the spirit and scope of the present disclosure.

The invention claimed is:

1. An atraumatic device for clamping a tissue, the device comprising:
   at least two oppositely polarized magnets, wherein the at least two magnets are electromagnets;
   a mounting structure for the at least two magnets;
   power source for providing power to the electromagnets;
   at least one electrical connector coupled to the power source and further coupled to at least one of the electromagnets, whereby power is provided by the power source through the at least one electrical connector to electrify at least one of the electromagnets, causing the electromagnets to clamp a tissue positioned therebetween; and
   at least one sensor operably coupled to at least one of the electromagnets, the at least one sensor operable to detect the level of clamping pressure upon a tissue positioned substantially in between at least two of the electromagnets.

2. The device of claim 1, further comprising at least one control mechanism operably coupled to the power source and the at least one sensor, the at least one control mechanism operable to regulate the level of power provided by the power source used to electrify at least one of the electromagnets.

3. The device of claim 2, wherein the at least one control mechanism directs the power source to maintain a present level of power when the clamping pressure detected by the at least one sensor meets or exceeds a predetermined threshold.

4. The device of claim 2, wherein the at least one sensor is operable to detect a strain in the tissue.

5. The device of claim 4, further comprising at least one control mechanism operably coupled to the power source, wherein the at least one control mechanism is operable to regulate the level of power provided by the power source based upon a level of strain detected in the tissue by the at least one sensor.

6. The device of claim 1, wherein the at least one sensor comprises multiple sensors operably coupled to at least one of the electromagnets.

7. The device of claim 6, wherein at least one of the multiple sensors detects clamping pressure and at least one of the multiple sensors detects strain in the tissue.

8. An atraumatic device for clamping a tissue, the device comprising:
   two oppositely polarized electromagnets, the two electromagnets being pliable so that the two electromagnets may flex and/or contour in respect to a tissue positioned substantially in between the two electromagnets;
   a mounting structure for the at least two electromagnets;
   whereby a magnetic force bias the two electromagnets toward each other thereby exerting a clamping pressure on the tissue;
   a power source for providing power to the electromagnets;
   at least one electrical connector coupled to the power source and further coupled to at least one of the two electromagnets, whereby power is provided by the power source through the at least one electrical connector to electrify at least one of the two electromagnets, causing the electromagnets to clamp a tissue positioned therebetween;
   at least one sensor operably coupled to at least one of the two electromagnets, the at least one sensor operable to detect the level of clamping pressure upon the tissue, and
   at least one control mechanism operably coupled to the power source and the at least one sensor, the at least one control mechanism operable to regulate the level of power provided by the power source used to electrify at least one of the at least two electromagnets;
   wherein the at least one control mechanism directs the power source to maintain a present level of power when the clamping pressure detected by the at least one sensor meets or exceeds a predetermined threshold.

9. An atraumatic device for clamping a tissue, the device comprising:
   at least one electromagnetic collar;
   a power source for providing power, the power source electrically coupled to the at least one electromagnetic collar by at least one electrical connector for providing power to the at least one electromagnetic collar, whereby power is provided by the power source through the at least one electrical connector to electrify the at least one electromagnetic collar, causing the at least one electromagnetic collar to clamp a tissue positioned therebetween; and
   at least one sensor operably coupled to the at least one electromagnetic collar, the at least one sensor operable to detect the level of clamping pressure by the at least one electromagnetic collar upon the tissue.

10. The device of claim 9, further comprising at least one control mechanism operably coupled to the power source and the at least one sensor, the at least one control mechanism operable to regulate the level of power provided by the power source used to electrify the at least one electromagnetic collar.

11. The device of claim 10, wherein the at least one control mechanism directs the power source to maintain a present level of power when the clamping pressure detected by the at least one sensor meets or exceeds a predetermined threshold.

12. The device of claim 10, wherein the at least one sensor detects a strain in the tissue.

13. The device of claim 12, wherein the at least one control mechanism is operable to regulate the level of power provided by the power source based upon a level of strain detected in the tissue by the at least one sensor.

14. The device of claim 9, wherein the at least one sensor comprises multiple sensors operably coupled to the at least one electromagnetic collar.

15. The device of claim 14, wherein at least one of the multiple sensors detects clamping pressure and at least one of the multiple sensors detects strain in the tissue.

16. An atraumatic device for clamping a tissue, the device comprising:
   at least one electromagnetic collar, wherein the at least one electromagnetic collar is pliable so that the at least one electromagnetic collar may flex and/or contour in respect to a tissue positioned substantially within the at least one electromagnetic collar;
   a power source for providing power, the power source electrically coupled to the at least one electromagnetic collar by at least one electrical connector for providing power to the at least one electromagnetic collar; whereby a magnetic force bias at least one electromagnetic collar thereby exerting a clamping pressure on the tissue; whereby power is provided by the power source through the at least one electrical connector to electrify the at least one electromagnetic collar, whereby causing the at least one electromagnetic collar to clamp a tissue positioned therebetween;
   at least one sensor operably coupled to the at least one electromagnetic collar, the at least one sensor operable to detect the level of clamping pressure by the at least one electromagnetic collar upon the tissue;

at least one control mechanism operably coupled to the power source and the at least one sensor, the at least one control mechanism operable to regulate the level of power provided by the power source used to electrify the at least one electromagnetic collar; and wherein the at least one control mechanism directs the power source to maintain a present level of power when the clamping pressure detected by the at least one sensor meets or exceeds a predetermined threshold.

17. A method of clamping tissue, the method comprising the steps of:
providing a clamping device, the clamping device comprising:
at least two oppositely polarized magnets; and
a mounting structure for the at least two magnets;
positioning the at least two magnets substantially around a tissue;
clamping the tissue by exerting a magnetic force between at least two of the at least two magnets on the tissue; and
detecting a clamping pressure on the tissue.

18. The method of claim 17, further comprising the step of regulating a magnetic force exerted on the tissue when the clamping pressure meets or exceeds a predetermined threshold.

19. A method of clamping tissue, the method comprising the steps of:
providing a clamping device, the clamping device comprising:
at least two oppositely polarized magnets; and
a mounting structure for the at least two magnets;
positioning the at least two magnets substantially around a tissue;
clamping the tissue by exerting a magnetic force between at least two of the at least two magnets on the tissue; and
detecting a strain within the tissue.

20. The method of claim 19, further comprising the step of regulating a force exerted on the tissue based upon the strain detected within the tissue.

21. A system for clamping tissue, the system comprising:
a clamping device, the clamping device comprising:
at least two oppositely polarized electromagnets; and
a mounting structure for the at least two electromagnets;
a power source for providing power to the at least two electromagnets;
at least one electrical connector coupled to the power source and further coupled to at least one of the two electromagnets whereby power is provided by the power source through the at least one electrical connector to electrify at least one of the two electromagnets, causing the at least two electromagnets to clamp a tissue positioned therebetween; and
at least one sensor operably coupled to at least one of the two electromagnets, the at least one sensor operable to detect the level of clamping pressure upon a tissue positioned substantially in between the two electromagnets.

22. The system of claim 21, further comprising at least one control mechanism operably coupled to the power source and the at least one sensor, the at least one control mechanism operable to regulate the level of power provided by the power source used to electrify at least one of the at least two electromagnets.

23. The system of claim 22, wherein the at least one control mechanism directs the power source to maintain a present level of power when the clamping pressure detected by the at least one sensor meets or exceeds a predetermined threshold.

24. A system for clamping tissue, the system comprising:
a clumping device, the clamping device comprising at least one electromagnetic collar;
a power source for providing power to the electromagnetic collar, the power source electrically coupled to the at least one electromagnetic collar by at least one electrical connector, whereby power is provided by the power source through the at least one electrical connector to electrify the at least one electromagnetic collar, causing the electromagnetic collar to clamp a tissue positioned therebetween; and
at least one sensor operably coupled to the at least one electromagnetic collar, the at least one sensor operable to detect the level of clamping pressure by the at least one electromagnetic collar upon the tissue.

25. The system of claim 24, further comprising at least one control mechanism operably coupled to the power source and the at least one sensor, the at least one control mechanism operable to regulate the level of power provided by the power source used to electrify the at least one electromagnetic collar.

26. The system of claim 25 wherein the at least one control mechanism directs the power source to maintain a present level of power when the clamping pressure detected by the at least one sensor meets or exceeds a predetermined threshold.

* * * * *